(12) United States Patent
Kropfeld et al.

(10) Patent No.: US 6,651,018 B2
(45) Date of Patent: Nov. 18, 2003

(54) METHOD FOR CORRECTING CALIBRATION VALUES IN A CALIBRATION TABLE OF COMPUTED TOMOGRAPHY APPARATUS

(75) Inventors: Helmut Kropfeld, Forchheim (DE); Karl Schwarz, Roth (DE)

(73) Assignee: Siemens Aktiengesellschaft, München (DE)

( * ) Notice: Subject to any disclaimer, the term of this patent is extended or adjusted under 35 U.S.C. 154(b) by 29 days.

(21) Appl. No.: 10/090,655

(22) Filed: Mar. 5, 2002

(65) Prior Publication Data

US 2002/0165686 A1 Nov. 7, 2002

(30) Foreign Application Priority Data

Mar. 16, 2001 (DE) .......................... 101 12 792

(51) Int. Cl.⁷ .................. G01N 37/00; G01N 23/00; G06F 19/00; A61B 6/00
(52) U.S. Cl. .................. 702/85; 702/106; 702/196; 278/4; 278/21; 278/9; 278/901
(58) Field of Search .................. 702/85, 106, 189, 702/190, 191, 195, 196; 378/4, 21, 19, 901

(56) References Cited

U.S. PATENT DOCUMENTS 6,163,759 A * 12/2000 Kita .......................... 702/85

* cited by examiner

*Primary Examiner*—John Barlow
*Assistant Examiner*—M. Walling
(74) *Attorney, Agent, or Firm*—Schiff Hardin & Waite

(57) ABSTRACT

In a method for correcting a calibration table $T(n,k)$ of a CT apparatus that contains calibration values, the CT apparatus having a detector system with $N \geq 2$ rows of detector elements following one another in the z-direction that include a first active row of detector elements in the z-direction and a last active row of detector elements in the z-direction, for correcting the calibration values of the aforementioned first and last active rows of detector elements, a reference vector $R(k)$ is produced, the error is determined with respect to the first and last active rows of detector elements, and the error $F(n,k)$ of the first and last active rows of detector elements is subtracted from the corresponding calibration values of the calibration table $T(n,k)$ for determining corrected calibration values $T_{cor}(n,k)$ with respect to the first and last active rows of detector elements.

13 Claims, 3 Drawing Sheets

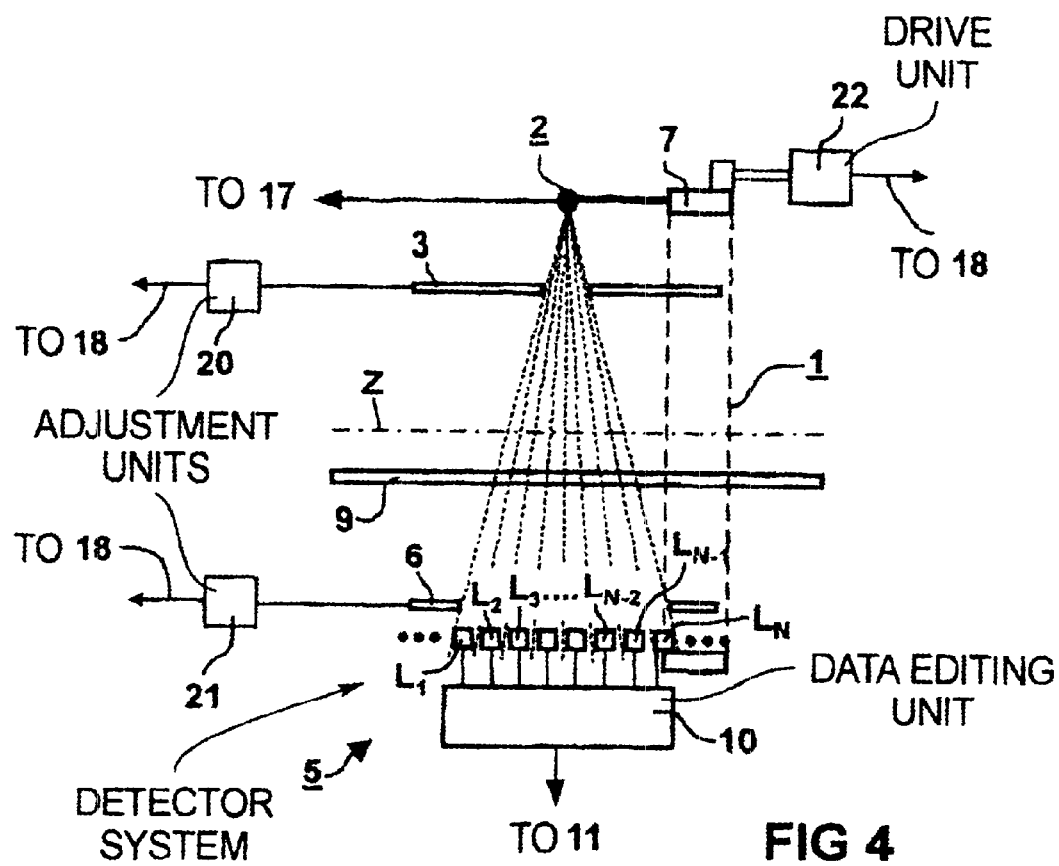

METHOD FOR CORRECTING CALIBRATION VALUES IN A CALIBRATION TABLE OF COMPUTED TOMOGRAPHY APPARATUS

BACKGROUND OF THE INVENTION

1. Field of the Invention

The present invention is directed to a method for correcting a calibration table of a (CT) apparatus that contains existing calibration values, the CT apparatus having a detector system formed by $N \geq 2$ rows of detector elements following one another in the z-direction, that include a first active row of detector elements in the z-direction and a last active row of detector elements in the z-direction.

2. Description of the Prior Art

In such CT apparatus, each detector channel has its own sensitivity, i.e., the electrical output signals of the respective channels are usually different in amplitude given the same incidence of X-ray quanta per channel. As used herein "detector channel" means the signal path from the detector element to the digitalization point where conversion to digital form occurs.

One purpose of calibration is to identify the individual sensitivities of the channels and to store corresponding calibration values in tables—the calibration tables—for later corrections of the measured values. Attenuation values would be undefined without these corrections. Since the calibration values represent the reference values of the radiation intensities without an attenuating subject, the calibration tables are also referred to as air tables or air calibration tables. Without calibration, the tomograms would be covered by pronounced ring artifacts.

Such calibration tables are required dependent on parameters such as slice thickness B, tube voltage U, rotation time T, a switchable pre-filtering, possibly two currents i and detector temperature $\theta$.

The number of possible parameter combinations of B, U, T and, possibly, i, $\theta$ is extremely high, so that the outlay for generating and storing corresponding calibration tables would be considerable. Moreover, all calibration tables would have to be updated with corresponding measurements at every re-calibration of the system —and such a recalibration can be necessary daily.

For time reasons, a separate calibration table is not produced for every individual parameter combination in a CT apparatus. It is conventional, for example, to produce a base table for each slice thickness B, this being calibrated daily. The other parameters are usually set to average values. The table that is utilized in all other parameter combinations is derived from the addition of a base table of the slice thickness B that has been set and one or more difference tables that contain the deviation relative to the modified parameters. The difference tables then need not be calibrated daily but only once in the factory or given a hardware replacement (for example, installation of a new x-ray tube).

In a single-line CT apparatus (detector with one line or row of detector elements), for example, the table for the parameter combination slice thickness B=1 mm, voltage U=140 kV, rotation time T=1 sec is composed of a base table for B=1 mm, U=120 kV and T=0.75 sec and of a voltage difference table for B=1 mm, U=140 kV and T=0.75 sec, as well as of a rotation time difference table for B=1 mm, U=120 kV and T=1 sec.

The above method in fact still requires some time but delivers good results for single-line CT apparatus.

In a multi-line CT apparatus, however, the problem arises that no accurate calibration is possible with respect to the outer rows, particularly with respect to the two outermost, active rows of detector elements, i.e. the first active row in the z-direction and the last active row in the z-direction.

SUMMARY OF THE INVENTION

An object of the present invention is to provide a method of the type initially described which enables an accurate calibration of a multi-line CT apparatus.

This object is inventively achieved in a method wherein the calibration values contained in the calibration table $T(n,k)$ with respect to the outer active rows of detector elements are corrected by producing a reference vector $R(k)$, and on the basis of this reference vector errors $F(n,k)$ of the calibration values with respect to the outer active rows of detector elements are identified, and corrected calibration values $T_{cor}(n,k)$ with respect to the outer active rows of detector elements are acquired by subtracting the identified errors from the corresponding calibration values. The calibration table $T(n,k)$ can be a base table $T_B(n,k)$ or a difference table $T_D(n,k)$.

The inventive method therefore enables an improved calibration of a multi-line CT apparatus because the calibration measurements for a multi-line CT apparatus in the outer, particularly in the two outermost, active rows are affected by time-variant errors that, for example, occur due to a non-reproducible diaphragm positioning, particularly of the detector-proximate diaphragms, due to aging processes or due to temperature effects.

When the calibration is based on a base table $T_B(k)$ and m=2 difference tables $T_{D1}(k)$ and $T_{D2}(k)$, the following applies ideally for an arbitrary row of detector elements for the corrected signal $S(k)$ acquired from the measured signal $M(k)$:

$$S(k)=M(k)-(T_B(k)+T_{D1}(k)+T_{D2}(k)), \text{ whereby}$$

S is the corrected signal,
M is the measured signal of a channel,
$T_B$ is the base table,
$T_{Dm}$: is the difference table m, and
k is the channel index.

Since, however, each measurement, i.e. the production of tables, is affected by the time-variant error $F(t,k)$ (t is time), the following in fact applies:

$$S(t,k)=M(k)+F(t,k)-(T_B(k)+F(t_3,k+T_{D1}(k)+F(t_1,k)+T_{D2}(k)+F(t_2,k))$$

or, in a first approximation:

$$S(k)=M(k)-(T_B(k)+T_{D1}(k)+T_{D2}(k))-2F(t_{2,k)},$$

i.e. the sum of the errors of the difference tables employed remains in a first approximation. This is true because the base table is in fact measured on the same day as the measurement itself and $(t \approx t_3) \sim F(t,k) \approx F(t_3,k)$ therefore applies. The difference tables, however, are measured together during the manufacture in the factor $(t_1 \approx t_2)$, for which reason $F(t_1,k) \approx F(t_2,k)$ applies.

Whereas the time-variant errors are negligible for inner active rows, the time-variant errors of the outer, particularly of the outermost, active rows, which would produce losses in image quality, are corrected by the inventive method,

DESCRIPTION OF THE DRAWINGS

FIG. 4 shows a further CT apparatus in an operating mode having a larger number of active rows of detector elements compared to FIGS. 2 and 3, in an illustration analogous to FIG. 2.

DESCRIPTION OF THE PREFERRED EMBODIMENTS

Figure 1:
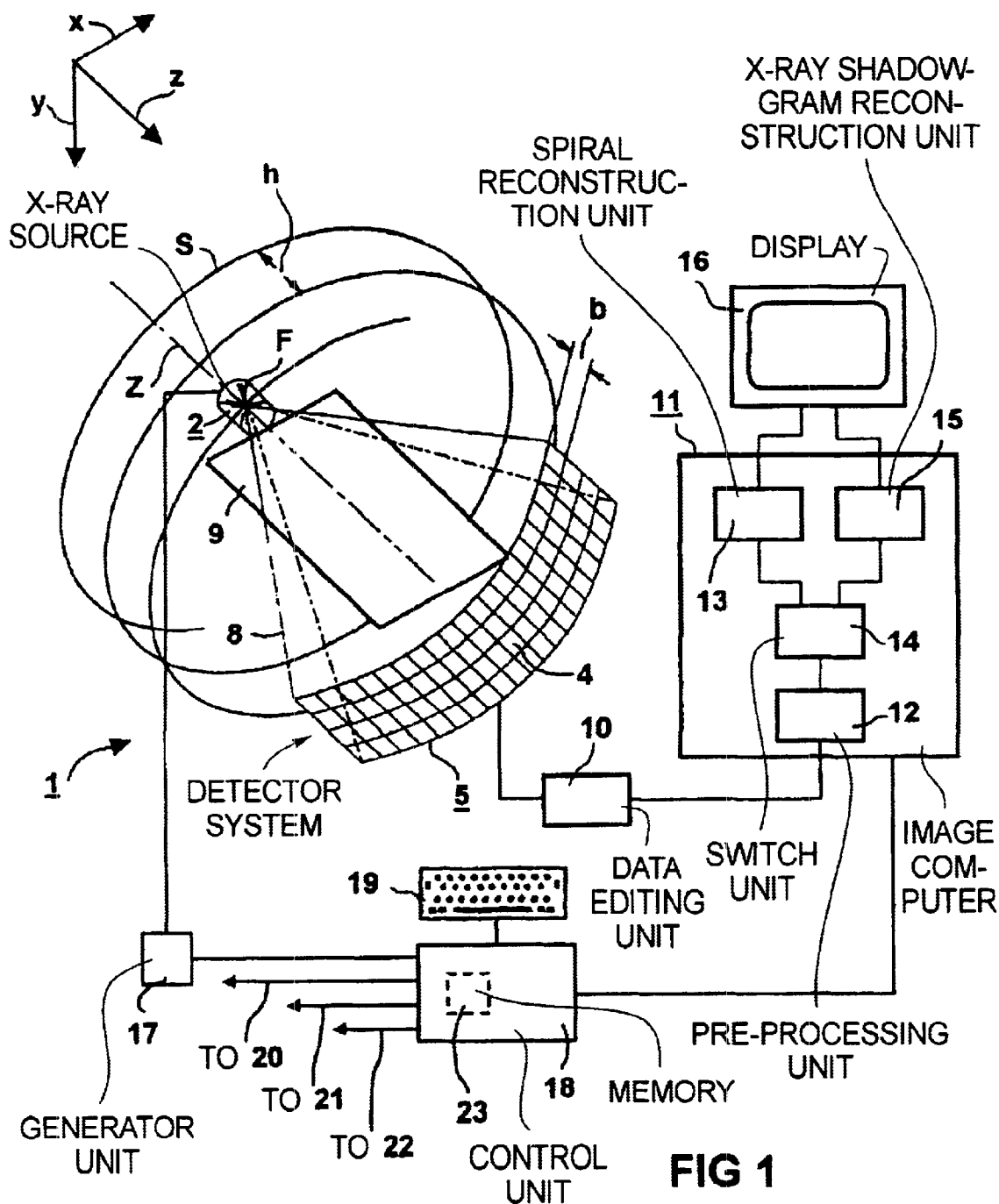
FIG. 1 is a schematic illustration of a CT apparatus having multiple rows of detector elements.
Figure 2:
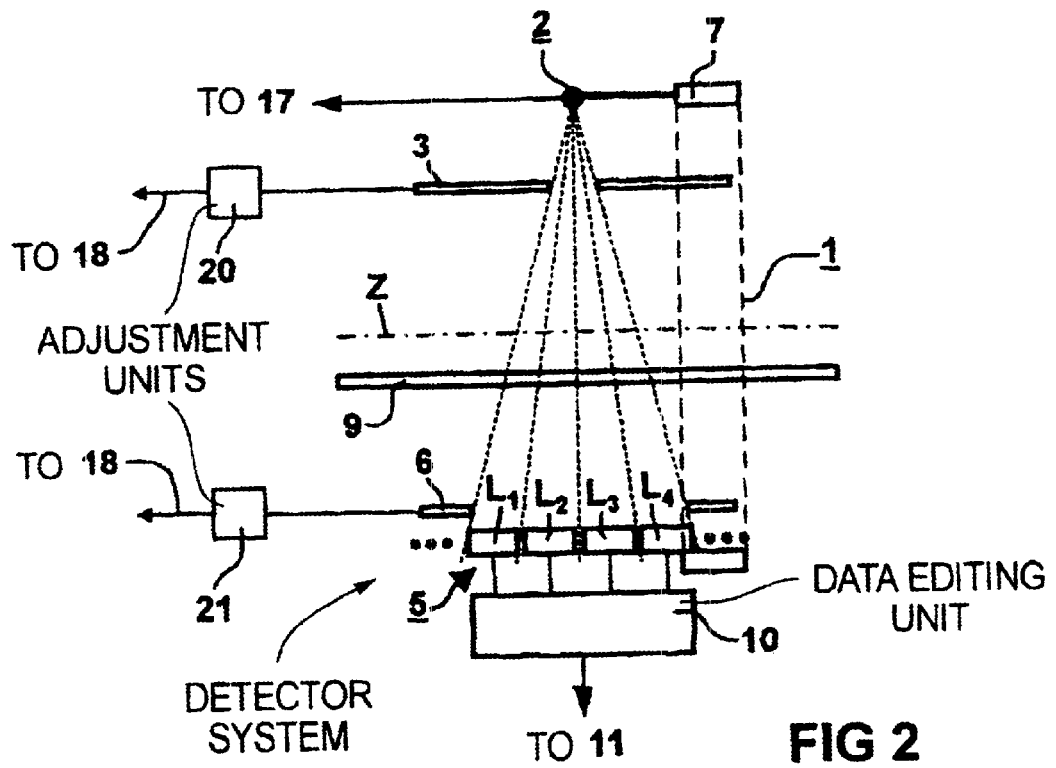
FIG. 2 is a longitudinal section through the apparatus according to FIG. 1 in a first operating mode.

FIGS. 1 and 2 show a CT apparatus of the third generation suitable for the implementation of the inventive method. The measuring arrangement thereof, generally referenced 1, has an x-ray source 2 with a source-proximate radiation diaphragm 3 (FIG. 2) in front of it and a detector system 5 fashioned as a planar array of multiple rows and columns of detector elements—one of these is referenced 4 in FIG. 1—with a detector-proximate radiation diaphragm 6 (FIG. 2) in front of it. For the clarity, only four rows of detector elements 4 are shown in FIG. 1. As indicated by the dots in FIG. 2, however, the detector system 5 has further rows of detector elements 4.

As can be seen from FIG. 2, the x-ray source 2 with the radiation diaphragm 3 and the detector system 5 with the radiation diaphragm 6 are attached to a live ring 7 opposite one another, such that a pyramidal x-ray beam that emanates from the x-ray source 2 during operation of the CT apparatus, and is gated by the variable radiation diaphragm 3, strikes the detector system 5, the edge rays of this x-ray beam being referenced 8. Corresponding to the cross-section of the x-ray beam set with the radiation diaphragm 3, the radiation diaphragm 6 is set such that only that region of the detector system 5 is enabled that can be directly struck by the x-ray beam. In the operating mode shown in FIGS. 1 and 2, these are four rows of detector elements 4, which are referred to below as active rows. The further rows indicated by the dots are covered by the radiation diaphragm 6 and therefore are not active.

Four active rows of detector elements 4 referenced $L_1$ through $L_N$ (line index N=1, 2, 3, 4) are present, each having the same width b in the exemplary embodiment, i.e. $L_1$ through $L_4$. Two outer, active rows thus are present, namely the first row $L_1$ in the z-direction and the last row $L_N$, i.e. $L_4$, in the z-direction, these having two inner, active rows $L_2$ and $L_{n\times1}$, i.e. $L_3$, neighboring them. Each row of detector elements 4 contains a total of K detector elements, whereby k=1 through K is what is referred to as the channel index.

The live ring 7 can be placed into rotation around a system axis Z with a drive unit 22 (shown in FIG. 4). The system axis Z proceeds parallel to the z-axis of a spatial rectangular coordinate system shown in FIG. 1.

The columns of the detector system 5 likewise proceed in the direction of the z-axis, whereas the rows, whose width b is measured in the direction of the z-axis and, for example, amounts to 1 mm, proceed transversely relative to the system axis Z and the z-axis.

In order to introduce an examination subject, for example a patient, into the beam path of the x-ray beam, a support mechanism 9 is provided that is displaceable parallel to the system axis Z, i.e. along the direction of the z-axis, with a synchronization between the rotational movement of the live ring 7 and the translational movement of the support mechanism 9 in the sense that the ratio of translation velocity to rotational velocity is constant. This ratio can be set by selecting a desired value for the feed h of the support mechanism 9 per revolution of the live ring 7.

A volume of an examination subject situated on the support mechanism 9 thus can be examined during the course of a volume scan, the volume scan being undertaken in the form of a spiral scan in the sense that a number of projections are registered from different projection directions with the measuring unit 1 per revolution of the measuring unit 1 with simultaneous rotation of the measuring unit 1 and translation of the support mechanism 9. In spiral scanning, the focus F of the x-ray source moves relative to the support mechanism 9 on a spiral (helical) path that is referenced S in FIG. 1.

The measured data for the individual projections are read out in parallel during the spiral scan from the detector elements 4 of each active row of the detector system 5 and are subjected to an analog-to-digital conversion in a data editing unit 10, are serialized and transmitted to an image computer 11.

After a pre-processing of the measured data in a pre-processing unit 12 of the image computer 11, the resulting data stream proceeds to a tomogram reconstruction unit 13 that reconstructs tomograms of desired slices of the examination subject from the measured data according to a known method (for example, 180LI or 360LI interpolation).

In order to be able to identify the position of a slice, with respect to which a tomogram is to be reconstructed, in the z-direction, an x-ray shadowgram can be reconstructed from the measured data in addition to tomograms. To this end, a portion of the measured data required for the reconstruction of an x-ray shadowgram of a desired projection direction is extracted with a shunt 14 from the data stream coming from the data editing unit 10—before this data stream proceeds to the tomograph reconstruction unit 13—and is supplied to an x-ray shadowgram reconstruction unit 15 that reconstructs an x-ray shadowgram from the extracted measured data according to a known method.

The tomograms or x-ray shadowgrams reconstructed respectively by the tomograph reconstruction unit 13 and the x-ray shadowgram unit 15 during the implementation of the spiral scan are displayed on a display unit 16, for example a video monitor, connected to the image computer 11. This display proceeds parallel to and synchronously with the spiral scan.

The x-ray source 2, for example an x-ray tube, is supplied with the necessary voltages and currents, for example the tube voltage U, by a generator unit 17. In order to be able to set this to the required values, the generator unit 17 has a control unit 18 with keyboard 19 allocated to it that allows the necessary settings.

The rest of the operation and control of the CT apparatus ensues with the control unit 18 and the keyboard 19, this being illustrated by the connection of the control unit 18 to the image computer 11.

Among other things, the number N of active rows of detector elements 4 and, thus, the position of the radiation diaphragms 3 and 6 can be set, for which purpose the control unit 18 is connected to adjustment units 20 and 21 (shown in 2, 3, and 4) respectively allocated to the radiation diaphragms 3 and 6. Further, the rotation time τ that the live ring 7 requires for a complete revolution can be set, this being illustrated by a control line to the drive unit 22 allocated to the live ring 7 (see FIG. 4) from the control unit 18.

It is thus possible to set different parameter combinations of the tube voltage U, the number N of active rows of detector elements 4 and the rotation time T of the live ring 7 for the operation of the CT apparatus according to FIGS. 1 and 2.

As already set forth, a base table exists for each parameter combination for the respective number N of active rows of detector elements 4 with average values for the tube voltage U and the rotation time T. Difference tables also exist for different tube voltages U and different rotation times T, but only the base tables are regularly measured, for example daily, whereas the difference tables are only occasionally measured, i.e. upon assembly of the CT apparatus in the factory or after the replacement of critical components.

The base and difference tables are stored in a memory 23 of the control unit 18. The memory 23 can be a separate memory within the control unit 18 or the memory 23 can be a memory area provided for storing the calibration values in a memory that is already contained in the control unit 18.

When, in the CT apparatus according to FIGS. 1 and 2, operation is to be carried out with, for example, the parameter combination N=4 corresponding to a slice thickness B=N*b=4*1 mm, tube voltage U=140 kV and rotation time T=1 sec, the table is composed of a base table $T_{B(N=4)}(n,k)$ for N=4, U=120 kV and T=0.75 sec and a voltage difference table $T_{D(U,N=4)}(n,k)$ for N=4, U=140 kV and T=0.75 sec, as well as a rotation time difference table $T_{D(T,N=4)}(n,k)$ for N=4, U=120 kV and T=1 sec.

After correction of the measured data M(n,k), the following is obtained in a first approximation for n=1 and n=N $$S(n,k)=M(n,k)-(T_{B(N=4)}(n,k)+T_{D(U,N=4)}(n,k)+T_{D(T,N=4)}(n,k))-2F(t_{2,n,k}),$$

rather than $$S(n,k)=M(n,k)-(T_{B(N=4)}(n,k)+T_{D(U,N=4)}(n,k)+T_{D(T,N=4)}(n,k)),$$

as should be theoretically operated, i.e. the sum of the errors of the difference tables employed remains in a first approximation.

In order, following the measurement of the calibration tables, to eliminate the time-variant errors of the calibration values of the outer active rows $L_1$ and $L_4$ (i.e. $L_N$) contained therein, a first correction mode is undertaken as explained below with reference to the example of an arbitrary difference table $T_D(n,k)$.

For producing a reference vector R(k), the calibration values of the inner active rows $L_2$ and $L_3$ (i.e. $L_{N-1}$) contained in the respective difference table are averaged:

$$R(k) = \frac{1}{(N-2)}\sum_{n=2}^{N-1}(T_D(n,k)),$$

whereby
n is the row index n=I through N
k is the channel index
N is the number of active rows, and
$T_D(n,k)$ is the difference table to be corrected Subsequently, the errors F(n,k) of the calibration values of the outer active rows, i.e. $L_1$ and $L_N$, are identified:

$$F(n,k)=T_D(n,k)-R(k) \text{ for n=1 and n=N}$$

For the purpose of smoothing, the errors F(n,k) identified in this way are low-pass-filtered:

$$K(n,k)=TP(F(n,k))$$

A low-pass filtering TP over k is thereby employed.

As a result of the low-pass filtering, only long-wave length components that, for example, are caused by faulty geometry, remain in the correction vector K(n,k).

In the last step for acquiring correction values $T_{Dcor}(n,k)$ for the outer rows $L_1$ and $L_N$, the correction vector K(n,k) is subtracted from the corresponding calibration values of the difference table $T_D(n,k)$:

$$T_{Dcor}(n,k)=T_D(n,k)-K(n,k) \text{ for n=1 and n=N}$$

Since all high-frequency components corresponding to a high-pass filtering HP complementary to the low-pass filtering TP, as well as the low-frequency component from the reference vector, are preserved, the following applies in reformulated fashion:

$$T_{Dcor}(n,k)=HP(T_D(n,k))+TP(R(k)),$$

it is clear therefrom that the time-variant errors are at least largely corrected for the outer active lines $L_1$ and $L_N$.

When, as in the parameter combination of the operating mode of CT apparatus shown in FIG. 2, more than two active rows of detector elements (N>2) are present, a second correction mode can be selected wherein $R(k)=T_D(n+1,k)$ for determining the error for n=1 and $R(k)=T_D(N-1,k)$ for determining the error for n=N is produced as reference vector.

This means that various reference vectors are employed for the two outer active rows $L_1$ and $L_N$, these reference vectors respectively being the calibration values of the inner active row $L_2$ and $L_{N-1}$ of detector elements neighboring the respective outer active row $L_1$ and $L_N$.

In a modification of the second correction mode that, in particular, is significant when more than two inner active rows are present (N>4), as in the case of FIG. 4, $$R(k) = \frac{1}{u}\sum_{n=2}^{u+1}(T_D(n,k))$$

is used for determining the error for n=1, and $$R(k) = \frac{1}{u}\sum_{n=N-u}^{N-1}(T_D(nk))$$

is used for determining the error for n=N as a reference vector, whereby u is the number of inner active rows whose calibration values are averaged. Preferably, u≦N/2 is set.

When, as in the parameterization of the operating mode of the CT apparatus shown in FIG. 2, more than two active rows of detector elements are present (N>2), a third correction mode likewise provides that $$R(k) = \frac{1}{2}(T_D(n+1,k)+T_D(N-1,k))$$

is produced as a reference vector.

This means that, as in the correction mode described first, a common reference vector is employed for the two outer active lines $L_1$ and $L_N$, namely the average of the calibration values of the inner active lines $L_2$ and $L_{N-1}$ of detector elements 4 respectively neighboring the outer active rows, In a modification of the third correction mode that, in particular, is significant when, as in the case of FIG. 4, more than two inner active rows are present (N>4), as an example, $$R(k) = \frac{1}{2}\left(\frac{1}{u}\sum_{n=2}^{u+1}(T_D(n,k)) + \frac{1}{u}\sum_{n=N-u}^{N-1}(T_D(n,k))\right)$$

is determined as a reference vector, whereby u is the number of inner active rows whose calibration values are averaged. Preferably, u≦N/2 is also set here.

Figure 3:
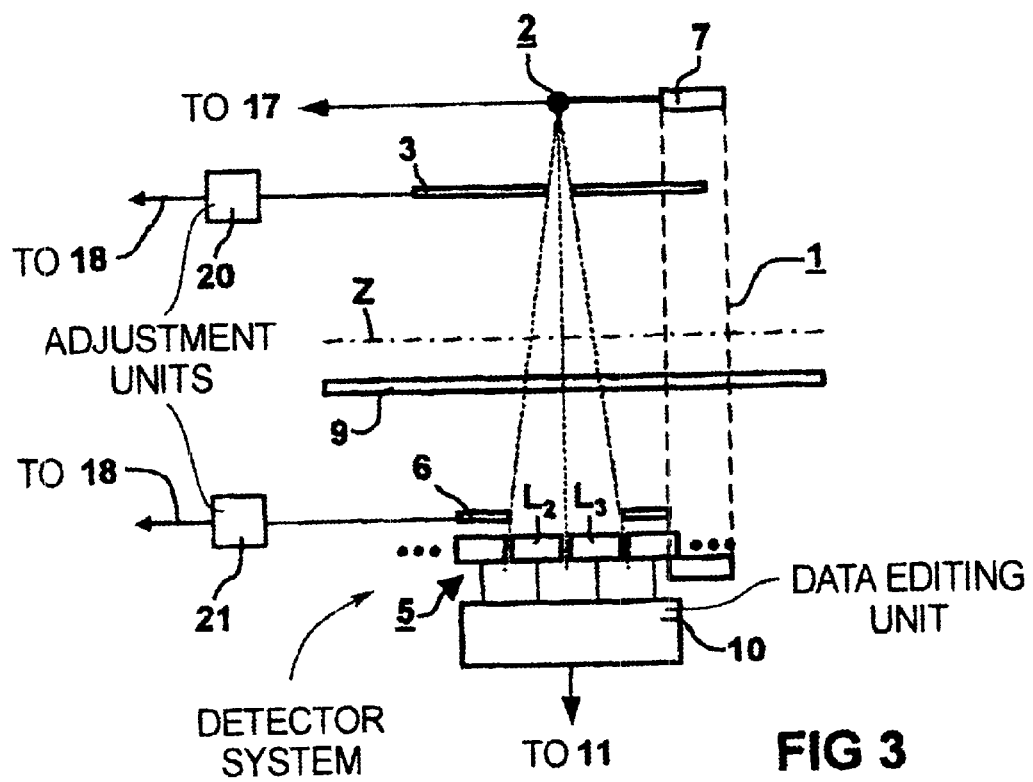
FIG. 3 shows a further operating mode of the CT apparatus of FIGS. 1 and 2 in an illustration analogous to FIG. 2.

The parameter combination for the operating mode of the CT apparatus according to FIG. 3 differs from that described above in that the radiation diaphragm 6 enables only two lines $L_1$ and $L_2$ of detector elements of the detector system 5, this corresponding to a number N=2 of active rows, so that the corresponding base table $B_{N=2}(n,k)$ for N=2, and a voltage difference table $D_{U,N=2}(n,k)$ for N=2, as well as a rotation time difference table $D_{T,N=2}(n,k)$ for N=2 are to be employed. In this case, $$R(k) = \frac{1}{2}(D(1,k) + D(2,k))$$

is produced as a reference vector of the respective difference table, i.e. the reference vector employed in common for the two outer active lines $L_1$ and $L_2$ is the average of the calibration values of the two outer active lines $L_1$ and $L_2$.

When a CT apparatus is operated with parameter combinations having a high number, for example N>4, of active rows the detector elements 4, it can be expedient, differing from the above-described exemplary embodiments, not to limit the correction of the calibration values to the two outermost active rows of detector elements, but to correct the calibration values of a number of outer active rows of detector elements, namely a number of rows a, respectively at both sides in the z-direction.

This is explained below for q=2 with reference to the example of FIG. 4, which shows a CT apparatus in an operating mode with N=8 active rows of detector elements.

In a preferred correction mode, the calibration values of the respective two sets of outer active lines of detector elements, i.e. the lines $L_1$, $L_2$ as well as $L_7$, $L_8$, i.e. $L_{N-1}$ and $L_N$, are corrected, with the reference vector being produced on the basis of the calibration vectors of the inner active lines, i.e. the lines $L_3$ through $L_6$:

$$R(k) = \frac{1}{(N-2q)}\sum_{n=q+1=3}^{N-q=6}(T_D(n,k))$$

As in the case of the above-described exemplary embodiments, the errors for the outer active rows are determined by subtraction of the reference vector from the correction values:

$F(n,k)=T_D(n,k)-R(k)$, for n=1, n=2, n=N-1 and n=N

One proceeds as in the case of the above-described exemplary embodiments for acquiring the correction vector and the corrected calibration values.

In a modification of the preferred calibration mode of the CT apparatus according to FIG. 4, a weighting of the reference vector ensues, the weighting in the case of the two outermost active lines $L_1$ and $L_N$ preferably being $G_1=1$, and the weighting in the case of the two other active lines $L_2$ and $L_{N-1}$ to be corrected is smaller than in the case of the two outermost active lines and, for example, is $G_2=\frac{1}{2}$:

$F(1,k)=T_D(1,k)-G_1 \cdot R(k)$ for n=1, $F(2,k)=T_D(2,k)-G_2 \cdot R(k)$ for n=2, $F(N-1,k)=T_D(N-1,k)-G_2 \cdot R(k)$ for n=N-1, and $F(N,k)=T_D(N,k)-G_1 \cdot R(k)$ for n=N, It is self-evident that more than two lines at each side of the detector system 5 can be incorporated into the correction.

In the case of the CT apparatus according to FIG. 4 as well the further correction modes described in conjunction with FIGS. 1 and 2 can be analogously applied.

In the registration of the base table or tables, moreover, a correction of calibration values of outer active rows of the detector elements ensues in one of the above-described correction modes, with the base table $T_B(n,k)$ being used instead of a difference table $T_D(n,k)$.

Instead of being implemented by the control unit 18, the method steps required for the correction of the calibration values can be implemented by the image computer 11. In the framework of the invention, moreover, there is also the possibility of exporting the calibration values from the CT apparatus onto an external computer, of correcting them therein and re-importing them into the CT apparatus.

The structure of the image computer 11 has been described above as though the pre-processing unit 12, the tomogram reconstruction unit 13, the shunt 14 and the x-ray shadowgram reconstruction unit 15 were hardware components. This can in fact be the case, but usually these components are realized by software modules that run on a universal computer provided with the required interfaces and that, in a departure from FIG. 1, also can assume the function of the control unit 18.

In the described exemplary embodiments, the relative motion between the measuring unit 1 and the support mechanism 8 was described as being generated by displacement of the support mechanism 9. However, there is also the possibility within the framework of the invention of leaving the support mechanism 9 stationary and instead displacing the measuring unit 1. Within the framework of the invention, there is also the possibility of generating the necessary relative motion by displacing the measuring unit 1 as well as the support mechanism 9.

A CT apparatus of the third generation was employed in conjunction with the above-described exemplary embodiments, i.e. the x-ray source 2 and the detector system 5 are displaced in common around the system axis Z during the image generation. However, the invention also can be employed in conjunction with a CT apparatus of the fourth generation, wherein only the x-ray source 2 is displaced around the system axis Z and interacts with a stationary detector ring, as long as the detector system 5 is a multi-row array of detector elements 4.

The inventive method also can be employed in a CT apparatus of the fifth generation, i.e. CT apparatus wherein the x-rays emanate not only from one focus but from a number of foci of one or more x-ray sources displaced around the system axis Z, again with a detector system 5 that is a multi-row array of detector elements 4.

The CT apparatus employed in conjunction with the above-described exemplary embodiments has a detector system 5 having detector elements 4 arranged in the fashion of an orthogonal matrix. However, the invention also can be employed in conjunction with a CT apparatus having a detector system with detector elements arranged in a planar array in some other way.

The above-described exemplary embodiments are directed to the medical application of the inventive method. In addition to being employed in medicine, however, the invention can be employed, for example, in baggage inspection or in the examination of materials.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for correcting a calibration table T(n,k) of a computed tomography apparatus wherein n is a row index of a detector system of the apparatus and k is a channel index of the detector system, said detector system comprising a plurality $N \geq 2$ of active rows of detector elements following one another in a z-direction that includes outer active rows comprising at least a first active row of detector elements in the z-direction and a last active row of detector elements in the z-direction, comprising the steps, for correcting the calibration values of the outer active rows of detector elements, of:

producing a reference vector R(k);

determining an error F(n,k)=T(n,k)−R(k) for the outer active rows, and subtracting the error F(n,k) for the outer active rows from calibration values of the calibration table T(n,k) for said outer rows to determine corrected calibration values $T_{cor}(n,k)$ for the outer active rows.

2. A method according to claim 1, comprising low pass filtering the error F(n,k) for the outer active rows before the subtraction from the calibration values of the calibration table T(n,k).

3. A method according to claim 1 wherein N>2 and comprising producing $$R(k) = \frac{1}{(N-2)} \sum_{n=2}^{N-1} (T(n,k))$$

as said reference vector for determining the error of the respective outermost active rows n=1 and n=N in the z-direction.

4. A method according to claim 1 wherein N>2 and comprising:

producing R(k)=T(n+1,k) as said reference vector for determining the error for the outermost active row n=1 at one side of the detector system, in the z-direction: and producing R(k)=T(N−1,k) as said reference vector for determining the error for the outermost active row n=N at an opposite side of said detector system in the z-direction.

5. A method according to claim 1 wherein N>2 and comprising:

producing $$R(k) = \frac{1}{u} \sum_{n=2}^{u+1} (T(n,k))$$

as said reference vector for determining the error for the outermost active row n=1 at one side of the detector system in the z-direction; and producing $$R(k) = \frac{1}{u} \sum_{n=N-u}^{N-1} (T(n,k))$$

n=N at an opposite side of the detector system in the z-direction wherein u is a number of inner active rows of said detector system between said outermost active rows.

6. A method according to claim 1 wherein N>2 and comprising:

producing $$R(k) = \frac{1}{2}(T(n+1,k) + T(N-1,k))$$

as said reference vector for determining the error of the respective outermost active rows n=1 and n=N in the z-direction.

7. A method according to claim 1 wherein N>2 and comprising:

producing $$R(k) = \frac{1}{2}\left(\frac{1}{(N-2)} \sum_{n=2}^{u+1} (T(n,k)) + \frac{1}{(N-2)} \sum_{n=N-n}^{N-1} (T(n,k))\right)$$

as said reference vector for determining the error of the respective outermost active rows n=1 and n=N in the z-direction.

8. A method according to claim 1 wherein N>2 comprising:

producing $$R(k) = \frac{1}{2}(T(1,k) + T(2,k))$$

as said reference vector for determining the error of the respective outermost active rows n=1 and n=N in the z-direction.

9. A method according to claim 1, comprising correcting calibration values at opposite sides of said detector system in the z-direction for respective pluralities q of outer rows, with $q \geq 1$.

10. A method according to claim 9, comprising:

producing $$R(k) = \frac{1}{(N-2q)} \sum_{n=1+q}^{N-q} (T(n,k))$$

as respective reference vectors for determining the error of the respective outermost active lines n=1 through n=q and n=N−q+1 through n=N in the z-direction.

11. A method according to claim 9 comprising identically weighting the reference vectors R(k) for determining the error of the respectively outermost active lines n=1 through n=q and n=N−q+1 through n=N in the z-direction.

12. A method according to claim 9 comprising differently weighting the reference vectors R(k) for determining the error of the respectively outermost active lines n=1 through n=q and n=N−q+1 through n=N in the z-direction.

13. A method according to claim 12, wherein the step of differently weighting the respective reference vectors R(k) for determining the error of the respective outermost active lines n=1 through n=q and n=N−q+1 through n=N in the z-direction comprises weighting the respective vectors R(k) increasingly higher from inside to outside of said detector system.

* * * * *